United States Patent [19]
Sorge et al.

[11] Patent Number: 5,589,155
[45] Date of Patent: *Dec. 31, 1996

[54] MUTAGENESIS TESTING USING TRANSGENIC NON-HUMAN ANIMALS CARRYING TEST DNA SEQUENCES

[75] Inventors: Joseph A. Sorge, San Diego; Jay M. Short, Encinitas, both of Calif.

[73] Assignee: Union Bank of California, N.A., San Franciso, Calif.

[ * ] Notice: The term of this patent shall not extend beyond the expiration date of Pat. No. 5,347,075.

[21] Appl. No.: 398,933

[22] Filed: Mar. 6, 1995

Related U.S. Application Data

[63] Continuation of Ser. No. 947,947, Sep. 18, 1992, abandoned, which is a continuation of Ser. No. 505,676, Apr. 5, 1990, abandoned, which is a continuation-in-part of Ser. No. 45,037, May 1, 1987, abandoned.

[51] Int. Cl.$^6$ ............................ A61K 49/00; C12N 15/00
[52] U.S. Cl. ...................... 424/9.2; 800/2; 800/DIG. 1; 435/172.3; 435/320.1; 435/6; 935/31; 935/77; 935/111
[58] Field of Search .................................. 800/2, DIG. 1; 435/172.3, 320.1; 935/31, 77, 111; 424/2, 9

[56] References Cited

U.S. PATENT DOCUMENTS 5,347,075  9/1994  Sorge ............................................ 800/2

*Primary Examiner*—Jasemine C. Chambers

[57] ABSTRACT

An assay for monitoring and assessing the mutagenic potential of agents which involves creating transgenic non-human animals carrying a test DNA-sequence or sequences that can be quickly recovered and examined for mutations following exposure to one or more suspected mutagenic agents.

6 Claims, 7 Drawing Sheets

Construction of p Blue MI–
FIG. 4
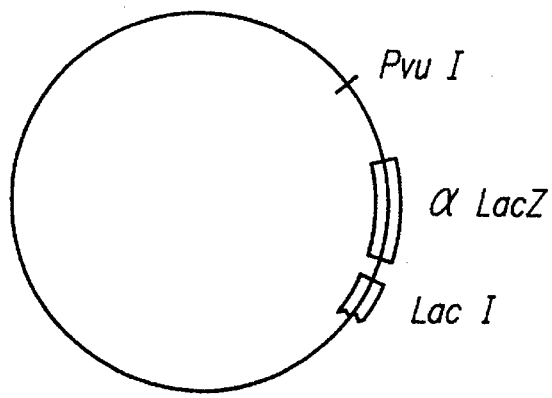
pBluescript SK–
Site directed mutagenesis
to introduce Ava III
restriction site
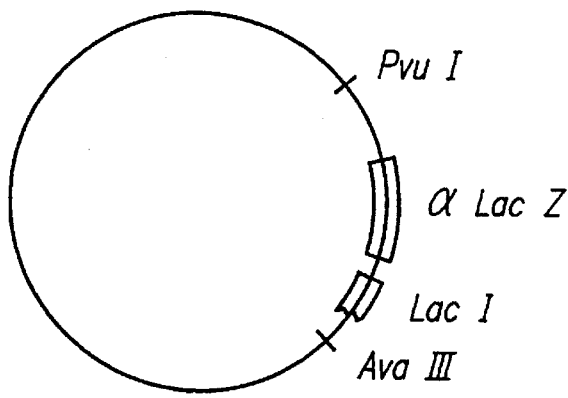
pBlueMI–

MUTAGENESIS TESTING USING TRANSGENIC NON-HUMAN ANIMALS CARRYING TEST DNA SEQUENCES

This is a continuation of application Ser. No. 07/947,947, filed Sep. 18, 1992 now abandoned; which is a continuation of application Ser. No. 07/505,676 filed Apr. 5, 1990, now abandoned; which is a CIP of application Ser. No. 07/045,037 filed May 1, 1987; which is now abandoned.

BACKGROUND OF THE INVENTION

1. Field of the Invention

This invention relates to transgenic animals and to tests for monitoring mutagenic agents in live animals. More specifically, this invention relates to the creation of transgenic non-human animals carrying test DNA sequences and to methods for monitoring and assessing the mutagenic potential of agents by exposing the transgenic animal to one or more suspected mutagens, and optionally recovering the test DNA sequence, and examining the test DNA sequence for mutations. Novel methods for increasing the efficiency of test DNA sequence recovery and rapid analysis of specific test DNA mutations are also described.

2. Description of Related Art

Various agents, such as radiation, ultraviolet light, synthetic chemicals, natural substances, and aberrations in genetic replication and repair can produce mutations in DNA. The results of a representative study indicate that as many as 60% of the cancers that develop in women and as many as 40% of those that develop in men result from avoidable exposure to mutagens from dietary intake. Vuoto et al., *Environ. Mutagen* 7:577–598 (1985). Exposure to environmental mutagens such as nitro-aromatic compounds found in automobile exhaust, chlorination by-products used in drinking water, and acrylamide and formaldehyde used extensively in industrial laboratories is also of major concern. Quantitative measurement of the effect of suspected mutagens is essential to control exposure to harmful agents. Additionally, whenever a new chemical, drug, or food additive, for example, is to be taken from the laboratory to the marketplace, it must be tested for its toxicity and cancer-causing potential. As a result, significant effort has gone into the development of assays that detect the mutagenic potential of various compounds.

Existing tests that assess the mutagenic potential of substances focus either on alterations of DNA in cultured cells or bacteria or alterations in the health of test animals. However, few tests that monitor alterations in DNA actually expose live animals to the agent to be tested. This is because it is very difficult to rapidly monitor alterations in the genetic code simultaneously in many different organs. Tests to detect these mutations must be very sensitive. They must be able to detect a single mutation amongst millions of normal genetic units. The difficulty of this task currently makes this approach for live animal studies prohibitively expensive as well as time intensive. Therefore, most current live animal genotoxicity tests use disease formation or large scale chromosomal alterations as an assay for gene alteration.

The problem of readily detecting small scale DNA alterations that are caused by potential mutagenic agents has generally been approached by performing studies on procaryotic or eukaryotic cells in culture (in vitro tests). The well-known Ames' test uses a special strain of bacteria to detect these mutations. Ames, et el., An Improved Bacterial Test System for the Detection and Classification of Mutagens and Carcinogens, *Proc. Nat. Acad. Sci.* 70:782–86 (1973). This test and many analogues that use other types of bacterial or animal cells permit the rapid screening of very large numbers of cells for the appearance of an altered phenotype. The appearance of this altered phenotypic trait reflects the occurrence of a mutation within the test gene. These tests are, however, insensitive to or nonspecific for many mutagens that result from metabolic activation of the agent being screened. Although attempts have been made to increase their sensitivity and specificity by activation of such metabolites with liver and other extracts it is noted that, for instance, the metabolites produced by these extracts are often not present at the same concentrations as in the live tissues of an animal. Metabolites that are only produced in other organs are not detected at all.

Eukaryotic cell lines have also been used to detect mutations. E.g.,., Glazer et el., Detection and Analysis of UV-induced Mutations in Mammalian Cell DNA using Lambda Phage Shuttle Vector., *Proc, Natl, Acad. Sci, U.S.A.* 83:1041–1044 (1986). In this test a target test gene, the amber suppressor tyrosine tRNA gene of *E. coli* in a bacteriophage shuttle vector, was integrated into a genomic host mammalian cell line by DNA transfection of cultured cells in vitro. After exposing the host cell line to putative mutagenic agents, test genes were reisolated, propagated in bacteria, and analyzed for mutations. Because the host is only a mammalian cell line and not a live animal, the test is incapable of accurately monitoring mutagenic metabolites of the agent being tested that are only produced at the appropriate concentrations by differentiated cells or the tissue of live animals.

A two year study by the NIH concluded that data obtained from four different prokaryotic and eukaryotic in vitro assays had only a 60% concordance with whole animal carcinogenicity studies. Tennant et al., *Science* 236:933–941 (1987). The study suggests that the high rate of error may result from potential variation in genetic susceptibility between in vitro systems and whole animals. For example, metabolites, frequently involved in activation of promutagens, are not present in in a vitro systems, allowing mutagenic potential to go undetected. In addition, differences in DNA repair mechanisms between prokaryotes and eukaryotes may account for some discrepancies in results.

Test genes and large scale screening assays used for in vitro assays are not available for live animal studies. Short of relying on longterm animal studies that detect phenotypic changes that require a long time to be identifiable, such as tumors, organ failure, coat color, etc., current tests do not provide a means for monitoring organ-specific mutations of DNA. Hence, there exists a need for a system that places a test DNA sequence within an animal and is subsequently assayed on a large scale for mutations. There also exists a need for methods that detect mutations caused by chemical metabolites of the agent being tested. To be most effective the system needs to be capable of monitoring genetic changes in as many tissues of an animal and as easily, rapidly, and inexpensively as possible.

The present invention, providing novel transgenic non-human mammals and methods utilizing such mammals for mutagenesis testing, satisfies these needs. More specifically, the present invention provides a sensitive screen for the mutagenicity of suspected agents and permits the monitoring of the mutagenic effects of such agents and the mutagenic effects of the metabolites of such agents. Additionally, the invention can permit the identification of the nature of the mutation, e.g., DNA transition, transversion, deletion, or a point or frameshift mutation. Further, the methods of the invention offer the significant advantage of being rapid to perform, thus permitting the identification of potential mutagens appreciably before other tests can be completed, and is inexpensive relative to other whole animal tests. And, the present invention substantially reduces the number of animals which must be used for mutagenesis testing.

SUMMARY OF THE INVENTION

The present invention provides novel transgenic non-human animals and methods for monitoring the mutagenic effects of potential mutagenic agents. In accordance with this invention, at least one copy of at least one target test DNA sequence is introduced into cells of a non-human mammal thereafter bred to produce test animals. Preferably, substantially all of the cells will contain the test DNA sequence. The test transgenic animal is then exposed to an agent suspected to be mutagenic and the test DNA sequence may be subsequently recovered from individual tissues of the transgenic animal. The test DNA sequence may be transferred into a microorganism, although such recovery and transfer is not requisite, and assayed for mutations, allowing rapid examination of multiple tissue specific genetic mutations. Other methods to monitor mutations in the test DNA need not rely on rescue and involve either direct examination of the test DNA in situ, PCR amplification of the test DNA, examination of RNA transcription products of the test DNA, or protein translation products of said RNA, or effects of said proteins or substrates for said proteins.

Theoretically, any animal suitable for mutagenic testing may be used as the starting organism. In order to allow for ubiquitous insertion of the novel test sequence, single cell animal embryos are harvested, although there may be other cells facilitating the uptake and ultimate ubiquitous presence of the marker DNA in cells of a differentiated animal.

In accordance with the invention, any number or variety of sequences coding for a phenotype or genotype that is detectable upon mutation may be used for introduction into the transgenic non-human mammals of the invention. Vectors capable of facilitating the recovery of the test DNA sequence from the host mammal cells, and capable of allowing replication and expression of the sequence in a bacterial host, are preferably used as carriers for the target test DNA sequence. Accordingly, the construct for such a vector and insert preferably should contain regions for excision from the mammal host genome, and regions that allow replication in a bacterial host cell, as well as regions that permit expression and assay of the test DNA sequence. If integration into the host genome is not required, desired regions that allow for replication of the test DNA sequence in the animal host cells should be present. Elbrecht, A., DeMayo, F. J., Tsai, M., and O'Malley, B. W. (1987), Episomal Maintenance of a Bovine Papilloma Virus Vector in Transgenic Mice, *Mol. Cell. Biol.* 7:1276–1279.

Further, in accordance with the invention, the test DNA sequence is introduced into the host mammal, preferably (but not necessarily) at the single-cell embryo stage, so as to provide the stable presence of the test sequence throughout cells of the differentiated animal. The use of chimeric animals is also contemplated herein. Typically, this involves the integration of the test DNA sequence into the mammal host genome, although methods that allow the test sequence to be stably and heritably present through the use of autonomously replicating vectors will also be useful. Elbrecht, A., DeMayo, F. J., Tsai, M., and O'Malley, B. W. (1987), Episomal Maintenance of a Bovine Papilloma Virus Vector in Transgenic Mice. *Mol. Cell. Biol.* 7:1276–1279. At the cellular level, this may be accomplished using the techniques of microinjection, electroporation, dielectrophoresis or various chemically mediated transformation techniques, all of which are well known in the art. At the differentiated tissue level, other techniques may be necessary.

Following the introduction of the test DNA sequence and integration into the genome or cell, the transgenic cell or cells must be allowed to differentiate into a whole organism. This may be accomplished, for example, by embryo implantation into pseudopregnant females, or by other techniques allowing maturation of transgenic embryos. Once such maturation and differentiation has occurred, the animal is assayed for the presence of the test DNA sequence. Typically this involves removing small portions of tissue from the animal and using standard DNA hybridization assay techniques to detect the presence of the test DNA sequence.

Transgenic animals carrying the test DNA sequence are thereafter bred and offspring carrying the test DNA sequence may be selected for mutagenesis testing. In accordance with the invention, the selected transgenic mammals are exposed to agents or substances in question under appropriate conditions. Such conditions will depend, for example, on the nature of the agent or substance, the purpose of the mutagenesis study and the type of data desired.

After exposure of test transgenic animals to the agent to be tested under the desired conditions, desired tissue may be removed from the test animal. Because in the preferred embodiment the test DNA sequence is present in essentially all tissues, the tissue type tested is not limited by the process of insertion of the test DNA sequence. Any desired tissue may be removed and assayed at the DNA, RNA, protein or substrate/product level, by various methods including, but not limited to, in situ hybridization to the DNA or RNA, PCR, protein or enzymatic assays (*PCR Protocols, A Guide to Methods and Applications.* eds. Innis, M. et al., Academic Press, Inc., 1990; Maniatis et al., *Molecular Cloning, A Laboratory Manual,* Cold Spring Harbor, N.Y. 1982).

Alternatively, genomic DNA may be purified from the tissue. The target test DNA sequence which is integrated may then be rescued from the total genomic DNA of the host. This may be accomplished by excising it from the host genome or by suitable procedures allowing separation by size, weight or charge density. The method of rescue is dependent upon whether test DNA sequence is inserted into the genome, and whether flanking regions allow for excision, or whether the test DNA sequence is part of a replicating element allowing for separation techniques.

The rescued test DNA sequences may then be transferred into and expressed by microorganisms suitable for large scale screening techniques. In a preferred embodiment, this involves excising the test DNA sequence vector from the genomic DNA by packaging the test DNA sequence with bacteriophage packaging techniques. This may require ligating the test DNA sequence into an appropriate vector or merely involve direct transformation into a microorganism.

Microorganisms containing the test DNA sequence vector are thereafter grown on indicator plates or in selective media. Those organisms having a phenotype indicating mutation of the test DNA sequence are considered to contain a mutated test DNA sequence. The ratio of those organisms expressing mutated phenotype of test sequences to the total number of organisms containing the test DNA sequence is a measure of the mutagenicity of the agent and metabolites of it present in the tested tissue.

Bacteriophage packaging techniques involve the use of bacteriophage-infected host cell extracts to supply the mixture of proteins and precursors required for encapsidating the bacteriophage DNA from exogenous sources. We have recently discovered that the rescue efficiency of the test DNA sequence can be significantly increased by eliminating the restriction systems in the strain of host microorganism used both for preparing the packaging extracts as well as those microorganisms used for plating to detect mutagenesis. Additionally, other recovery systems, e.g., DNA transformation of isolated genomic DNA, would be improved by removed of such restriction systems or activities.

By removing these restriction systems which recognize and deactivate foreign DNA, rescue efficiencies may be increased up to at least 12,000 pfu/µg genomic DNA. These rescue efficiencies enable several million target genes from each tissue to be analyzed, generating a large number of data points and resulting in a significant reduction in the numbers of animals required for mutagenesis testing with greater statistical significance.

Accordingly, the integrated target test DNA sequence is, preferably, rescued from the total genomic DNA of the host mammal using a lambda packaging extract deficient in restriction systems which recognize and deactivate foreign DNA. The rescued test DNA sequences may then be transferred into and expressed by restriction system deficient microorganisms.

Alternatively, a shuttle vector system can be constructed which provides rapid analysis of test DNA sequence. The test DNA sequence may be contained within a system which allows excision and recircularization of the test DNA sequence, which system is contained by a bacteriophage derivative genome. Following rescue of the bacteriophage genome containing test DNA sequence using packaging extracts, the test DNA may be further excised from the bacteriophage genome and recircularized to provide for rapid mutation analysis.

Further, the present invention contemplates the performance of mutagenesis testing by examining the phenotypes of cells containing the test DNA sequence without recovery of the test DNA sequence from the cell. This may be accomplished by the sectioning of tissues of the transgenic mammal of the invention, after exposure to a potential mutagenic agent, and assaying the genotype of phenotype of the test DNA sequence by in situ hybridization or, e.g., by staining of the tissue sections.

Figure 1:
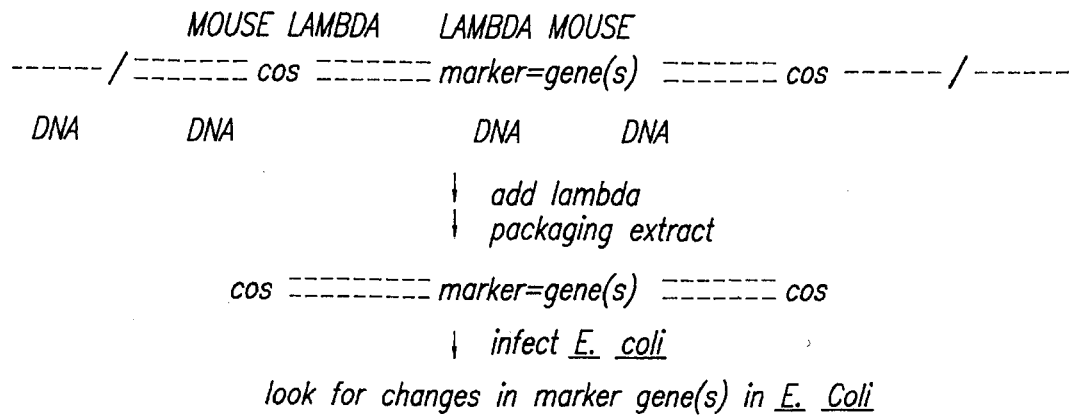
FIG. 1

This drawing is a diagram of a method for recovering mutagenized marker genes from transgenic mice.

FIG. 2

This drawing is a diagram of a method for recovering and analyzing mutagenized marker genes from transgenic mice.

FIG. 3

This drawing is a restriction map of clones recovered during mutagenesis testing.

FIG. 4

This drawing is a diagram of the construction of plasmid pBlueMI—.

FIG. 5

This drawing is a diagram of the construction of plasmid placI$^q$.

FIG. 6

This drawing is a diagram of the construction of plasmid pInt.1.

FIG. 7

This drawing is a diagram of the construction of plasmid pPrelaqZ.

FIG. 8

This drawing is a diagram of the construction of the lambda LIZ Alpha vector.

DESCRIPTION OF THE PREFERRED EMBODIMENT

The following description provides details of the manner in which the embodiments of the present invention may be made and used in order to achieve the rapid recovery and examination of test DNA sequences from transgenic animals. This description, while exemplary of the present invention, is not to be construed as specifically limiting the invention. Accordingly, variations and equivalents, now known or later developed, that would be within the purview of one skilled in this art are to be considered to fall within the scope of this invention, which is limited only as set forth by the appended claims.

A. DNA Test Sequence

The test sequence DNA can, theoretically, contain any number or variety of genes or other identifiable test DNA sequences. In the prototype described herein, an *E. coli* bacteriophage lambda genome has been engineered to carry lacZ, a beta-galactosidase test DNA sequence. Lambda shuttle vectors L2B (46.5 kb) or C2B (48.0 kb) may be used. The genotype of the modified lambda genome L2B is Lac5 delta (shind III lambda 2–3•) srI lambda 3–5• cI857 sXhL lambda 1• sScII lambda 4•. Before injecting it into mouse embryos as described below, this lambda DNA was diluted to a concentration of 10 micrograms per milliliter and the cos ends were annealed and ligated under conditions predominantly forming circular lambda phage monomers. Maniatis et al., *Molecular Cloning, A Laboratory Manual*, pp. 109–110, 383–389 (Cold Spring Harbor, N.Y. 1982).

In addition, a variation of L2B may be constructed that contains a plasmid sequence that can be readily excised from the lambda phage and contains the lacI repressor gene. This variation has several advantages. First, as discussed below, physical identification of phage carrying mutations will be facilitated since they will grow as blue plaques on a white background in the presence of X-gal (5-bromo-4-chloro-3-indolyl-β-D-galactopyranoside) without IPTG (isopropylβ-D-thiogalactopyranoside). This advantage will also simplify and reduce the cost of the assay since it will permit an increase in the density of phage per plate. Additionally, the lacI genetic system of *E. coli* are the first systems that conveniently permitted the study of large numbers of mutations within procaryotes at the DNA level (Miller et al., *J. Mol. Biol.* 109:275–302 (1977), Coulondre and Miller, *J. Mol. Biol.*, 117–275–302 (1977), Schaaper, *J. Mol. Biol.* 189:273–284 (1986)), and the use of lacI will provide a test gene with, significant historical mutational data for comparison between mutagenesis assays.

B. Creation of a Transgenic Animal

Mice were used as the test animal. (Hogan et al., *Manipulating the Mouse Embryo: A Laboratory Manual*, Cold Spring Harbor Laboratory, 1986). Single cell mouse embryos were harvested from female mice that were impregnated the evening before. The embryos were treated with hyaluronidase and briefly cultured in M16 medium. The embryos were transferred to M2 medium on a microscope glass depression slide. The embryos were observed with a 40X objective and a 10X eyepiece using a Nikon Diaphot microscope equipped with Hoffman optics. The embryos were held in place with a holding piper that had been rounded with a microforge. The positions of both the holding pipets and the injection pipers were controlled with micromanipulators. DNA as described above was loaded in the injection piper at a concentration of 1 to 10 micrograms per milliliter. Approximately one picoliter, as judged by a refractils change (Hogan et al., supra) of the pronucleus, of DNA solution was injected into the male pronucleus.

After DNA injection, the embryos were transferred to M16 medium and incubated at 37° C. in a 5% $CO_2$ atmosphere for one to two hours. Lysed embryos were discarded and embryos that appeared normal were transferred to one of the fallopian tubes of pseudopregnant foster mothers. The transfers were performed under a dissecting microscope using general anesthesia (avertin).

After birth, newborn mice were kept with their foster mothers for 2 weeks, at which point they were then weaned and screened for DNA integration. A 2 cm portion of the tail was removed and homogenized in 2 ml of a solution of 0.1M NaCl, 50 mM Tris-HCl, pH 7.5, lmM EDTA for short duration, but long enough to disrupt cell and nuclear membranes. The homogenized tissue was treated with 50 U/ml RNaseA and 0.1% SDS for 15 minutes at 37° C. The mixture was exposed to Proteinass K digestion for 3 hours at 55° C. followed by three extractions with phenol/chloroform. DNA was then precipitated by the addition of ethanol. After resuspending the precipitated DNA in 10 mM Tris pH 8.0, 0.5 mM EDTA, some of it was digested with BamHI endonuclease and electrophoresed through an 0.8% agarose gel. The DNA was denatured by soaking the gel in 1.5M NaCl, 0.5M NaOH for one hour and then neutralizing the DNA by soaking it in 1.5M NaCl, 0.5M Tris, pH 7.4 for 30 minutes. The gel was then soaked in 10X SSC for one hour. The DNA was then transferred from the gel into a nitrocellulose filter by the method of Southern, as described in Maniatis, supra.

The filter with transferred DNA was hybridized overnight with $^{32}p$ labeled lambda DNA prepared, according to standard procedures, by the method of nick translation. Maniatis, supra. Following this overnight hybridization, the filter was washed in 0.1xSSC, 0.1% SDS at 50° C. and Kodak XAR film was exposed to it in order to identify lambda DNA present within the mouse genome. Lambda DNA, used as standards, that had been electrophoresed alongside the mouse genomic DNA were compared in intensity to the transgenic mouse DNA hybridized to the $^{32}p$ labeled lambda DNA to estimate the number of copies of test DNA per mouse cell. Numerous transgenie animals have been produced and identified by this technique.

Newborn mice tested for the presence of the test DNA sequence by the tail-blotting procedure (Hogan, et al., *Manipulating the Mouse Embryo: A Laboratory Manual*, pp. 174–183 Cold Spring Harbor Laboratory, 1986) were found to carry the test DNA sequence in DNA isolated from their tails. Eight weeks after birth these transgenic mice were mated and their progeny were examined for the test DNA sequence. Approximately 50% of the resulting offspring carried the test DNA sequence, demonstrating that the original transgenic mice carried the test DNA sequence in their germ line and that this sequence was inherited normally. While transgenic lines having approximately one copy of the test DNA sequence per cell can be obtained, it will be understood by one skilled in the art that multiple copy numbers per cell are obtainable and may be useful for many different applications.

C. Mutagen Treatments

Six to eight week old transgenic male mice were treated on day 1 and day 4 by intraperitoneal injection of either 125 or 250 mg N-ethyl-N-nitrosourea (EtNu), per kg body weight. Control animals were injected with 100 mM phosphate buffer at 10 ml/kg body weight. Tissues were collected two hours after final injection.

D. Recovery of the Test DNA Sequence and Mutagenesis Testing

In the embodiment described here, rescue of the marker DNA sequence was accomplished by containing it within a lambda bacteriophage genome. The entire lambda bacteriophage genome is excised from the mouse chromosome by the in vitro packaging extract. The packaging extract recognizes the cos sites of the integrated lambda DNA and packages the sequences between the cos sites into lambda phage particles, as shown in FIG. 1.

The test DNA sequence may be found within the genomic DNA purified from any tissue of the transgenio mouse. Since the test DNA sequence is contained within a lambda phage genome, it can be excised away from the remainder of genomic DNA by using a lambda phage packaging extract. Packaged lambda phage such as L2B or C2B, may then be plated on *E. coli* cells for further evaluation.

Plating bacteria, β-galactosidase deficient *E. coli* are grown in 1X TB (5 g/L NaCL, 10 g/L trypone) supplemented with 0.2% maltose and 10 mM $MgSO_4$ overnight at 30° C. Cells are harvested by centrifugation and resuspended in 10 mM $MgSO_4$ in preparation for plating (Maniatis, supra).

In a typical experiment, 1–5 µg of genomic DNA are exposed to in vitro lambda phage packaging extract and incubated for 2 hours at room temperature. The packaging reaction is then diluted in 500 µl SM buffer (100 mM NaCL, 8 mM $MgSO_4$ 50 mM Tris, pH 7.5, and 0.01% gelatin) and incubated with the above described bacteria (2.0 mL of $OD_{600}$=0.5), and then plated onto NZY/agar Nunc Bioassay Dishes (245 mm×245 mm×20 mm) with molten top agar containing 1.25 mg/mL X-gal and 2.5 mM IPTG at a density of less than 20,000 pfu per plate. The plates are incubated overnight at 37° C.

For the lambda genomes containing the β-gal (not the lacI) gene, in the presence of X-gal (5-bromo-4-chloro-3-indoyl-β-D-galactopyranoside) and IPTG, the phage plaques turn blue if the beta-galactosidase sequence within the lambda genome has not mutated. However, a white plaque or faint blue plaque on the petri dish is evidence that a mutation in the beta-galactosidase sequence has, for example, altered the reading frame, altered essential codons, or has created stop codons in the sequence. These white or faint blue plaques will be scored as positive for mutations and they can be plaque purified and saved for further analysis. The ratio of white or faint blue to blue plaques minus background (mutation rate from non-mutagenized animals or tissues) will indicate the mutagenesis potency of the agent being tested when compared with DNA extracted from mice that have not been treated with potentially mutagenic agents.

E. Methods for Increasing Efficiency of Test DNA Sequence Rescue

1. Demethylation

It is anticipated that test DNA sequence rescue efficiency can be influenced by the state of CpG methylation in the mouse chromosome. Highly methylated DNA may not be efficiently excised by lambda packaging extract, presumably because of inhibition of cleavage at the cos sites, inhibition of expression of lambda genes encoded on lambda phage, or restriction by *E. coli* restriction systems. This may be alleviated by placing transcriptional enhancers, promoters and/or other regions of the DNA which inhibit methylation near critical sites such as the cos site to reduce CpG methylation. The drug 5'-azacytidine can also be used to reduce the level of DNA methylation in the target cells prior to DNA purification and rescue. Jaenisch, R., et al., *Proc. Natl. Acad. Sci. U.S.A.* 82:1451–1455 (1985). In such a procedure, fibroblast cell lines are obtained from organisms containing the test DNA sequence of interest. Adams, R. L. P., *Cell Culture for Biochemists*, pages 68–83 (1980 Elselvier/North Mollan Biomedical Press). The cells are exposed in vitro at 37° C., within 50 μM 5'-azacytidine supplementing the culture medium. Upon DNA replication, the daughter DNA loses its CpG methylation, which eliminates the methylation of sites, in the target vector, where the target vector is a lambda phage. The DNA from these fibroblasts is then exposed to in vitro packaging extract, as previously described.

Alternatively, organisms containing the test DNA sequence can be directly injected with a 1 mg/ml solution of 5'-azacytidine in 0.15M NaCl. This is done over a period of at least about 4 days, with a total of 400 μg administered. Jaenisch, supra. After this treatment, DNA can be extracted from various tissues and packaged as before.

2. Removal of Packaging Extract and Plating Strain Restriction Systems

We have determined that the efficiency of test DNA sequence recovery is dependent on the genotype of both the bacterial strain used to generate the packaging extract as well as the plating strains used for mutagenesis testing. This is due to host-controlled restriction systems that enable a bacterial cell to identify and inactivate foreign DNA by endonuclease cleavage. DNA is susceptible to restriction by the endonucleic activity of the host unless it is protected by modifications, such as methylation of specific nucleotides. While methylation of specific nucleotides usually serves to protect DNA from restriction by the endonucleolytic activity of the host, methylaltion at some DNA sequences actually confers sensitivity to restriction. One example, the mcrB restriction system of *E. coli* K-12, is responsible for the biological inactivation of foreign DNA that contains 5-methylcytosine residues. Ross et al., *Journal of Bacteriology* 171:1974–1981 (1989).

There are a number of restriction/methylation systems endogenous to *E. coli* which are capable of inactivating foreign DNA by endonuolease cleavage. The most widely known systems are hsd (Bickle, T. *Nucleases* p. 85, Cold Spring Harbor Lab., Cold Spring Harbor, N.Y. 1982), mrr (Heitman, J. et al., *J. Bacteriol.* 169:3243–3250 (1987)), mcrA (Raleigh et al., *PNAS* 83:9070–9074 (1986)) and mcrB (Raleigh, supra). The hsd system works by selectively restricting DNA that is not protected by adenine methylation at the N-6 position in the sequence, $A^{6me}$ACNNNNNNGTGC or $GC^{6me}$-ACNNNNNNGTT. The mrr system also involves adenine methylation, however, in this case the methylation does not serve to protect the DNA, but serves to make the DNA vulnerable to the restriction system. The systems mcrA and mcrB are similar to mrr in that they recognize and restrict methylated DNA. However, these two systems differ from mrr in that they recognize methylated cytosine. Further, the mcrB function is provided by the products of at least two genes, mcrB and mcrC (Ross et al., *J. Bacteriol*, 171:1974–1981 (1989)). The recognition sequences for mcr and mrr are contemplated in the literature, but precise sequences are as yet unknown.

We found that efficiency of recovery of the lacZ construct from the transgenic animal genome was increased without the use of 5-azacytidine, by using lambda packaging extracts and *E. coli* plating strains lacking restriction systems that cleave eukaryotic DNA. By removing these restriction systems, rescue efficiencies have been increased up to at least 12,000 pfu/μg genomic DNA. Of course, one skilled in the art will recognize that "removal" of these restriction systems may be effected by deleting or inhibiting the activity of these restriction systems, and the term "restriction system deficient" includes, but is not limited to, removal of the restriction systems by either method. In addition, naturally occurring strains of *E. coli* that are deficient in these restriction systems may be isolated and used.

Identification of the genes responsible for the *E. coli* restriction systems was achieved by examination of the inhibitory effect of certain *E. coli* strains on the ability to recover lambda phage. Isolation of the responsible genes was achieved through the use of interrupted matings and P1 transduction. An approximately 200 kb region of DNA in *E. coli* K-12 was found to produce an inhibitory effect on the plating efficiency of the rescued vector. Further, the region responsible for decreasing rescue efficiency was found to be near 98 minutes in the *E. coli* K-12 genetic map (Bachmann, B. *E. coli and S. Typhimurium: Cellular and Molecular Biology*, eds. Nejdhart et al., ASM, WA, DC, 1987) in the approximately 2.6 kb mcrB region containing mcrB and mcrC.

The comparison of the rescue efficiency using *E. coli* strains with different restriction genotypes is shown in Table 1. The bacterial strains listed in Table 1 are available from the following source or reference: ED8767 (Ishiura, M. et al., *Anal. Biochem.*, 176:117–127 (1988); ER1451 (New England BioLabs, Beverly, Mass.); LCK8 (B. Bachman, Yale *E. coli* Center); NM621 (N. Murray, Univ. of Edinburgh); K802, LE392, NM554, PLK-A, PLK-17, Y1088, *E. coli* C, Sure (Stratagens, LaJolla, Calif.)). Strain RR1-A and K-12ΔmcrB are constructed as described below.

Strain RR1-A is constructed with strain RR1 (Miniatis, supra) (relevant genotype=mcrA+, ($tet^s$)) as the recipient and any *E. coli* K-12 strain that carries a Tn10 (tetracycline resistant) in (or near) the mcrA gene (relevant genotype= mcrA:Tn10($tet^R$)) as the donor. Step 1: A P1 lysate is made from the *E. coli* K-12 strain described above. Step 2: RR1 is transduced (Miller, J., *Experience in Molecular Genetics*, Cold Spring Harbor Lab., Cold Spring Harbor, N.Y. (1972)). Step 3: Tetracycline resistant colonies are selected and purified. Step 4: Loss of tetracycline resistance is selected for on Bochner plates (Bochner, B. R., et al., *J. Bacteriol.*, 143:926–933 (1980)), and colonies are purified. Step 5: Lack of mcrA restriction activity is tested by comparing transformation efficiency of unmethylated pBR322 versus pBR322 that has been in vitro methylated by HpaII methylass (Raleigh, supra). A mcrA+ strain will show a greatly reduced efficiency with the methylated plasmid. If mcrA activity is absent, this strain is then called RR1-A.

Strain K-12 amcrB is constructed using two donor *E. coli* K-12 strains with the relevant genotypes mcrB::Tn10(tet$^R$), mrr::Tn5(Kan$^R$) and mcrA::Tn10(tet$^R$) and a recipient *E. coli* K-12 with the relevant genotype recA+, tet$^S$. Steps 1–5: Perform steps 1–5 as described for construction of RR1-A. In step 2, transduce any *E. coli* K-12 recA+ strain. Step 6: Make a P1 lysate from an *E. coli* K-12 strain that carries a Tn10(tet$^R$) in the mcrB gene. The strain should also have a Tn5(kan$^R$) in the mrr gene. Step 7: Transduce the K-12 recA+(tet$^S$) strain. Step 8: Select for tet$^R$ colonies. Purify one colony that is also kan$^R$. Step 9: Select for loss of tet$^R$ on Bochner plates (Bochner, supra). Step 10: Purify several colonies and test for sensitivity to tetracycline and kanamycin. Select colonies that are both tet$^S$ and kan$^S$. Step 11: Test for lack of mcrB restriction activity as done for the mcrA test, however in this case, the pBR322 should be vitro methylated by AluI methylase (Raleigh, supra; Ross, supra). A mcrB+ strain will show a greatly reduced efficiency with the methylated plasmid. Test for mrr restriction activity by comparing plating efficiency of lambda versus lambda which has been in vivo methylated by Pst I methylase (Heitman, supra). An mrr+ strain will show reduced efficiency with the methylated lambda. Test for hsdR restriction activity by comparing plating efficiency of lambda versus lambda which has been in vito methylated by hsdM methylase (Wood, W., *J. Mol. Biol.* 16:118–133 (1966); Adams, *Bacteriophages*, New York: Interscience 1959; Bickle, supra, at pp. 95–100). An hsdR+ strain will show reduced efficiency with unmethylated lambda. If a strain (purified colony) lacks all restriction activity mcrA, mcrB, mrr, hsdR and was constructed by this method, it should then contain a deletion throughout the mcrB region (ΔmcrB). It will then also very efficiently plate lambda that has been rescued from the mouse. This strain is called K-12ΔamcrB.

The "Δ" symbol in Table 1 indicates that the strain contains a large deletion in the mcrB region. All other mcrB-strains listed are K-12 derivatives believed to contain a small mutation in the mcrB region, with the exception of *E. coli C* which does not contain the K-12 mcrB region, and RR1-A which carries the wildtype mcrB locus of *E. coli B*. It is known that all of these strains plate control L2B phage (amplified in hsdM+ *E. coli* K-12 rather than rescued from the mouse) with equal efficiency (within 1–4 fold). Rescued L2B phage were recovered from the mouse genome using mcr—*E. coli* K-12 lambda packaging extracts (Gigapack II—Stratagene, La Jolla, Calif.). A "+" plating efficiency of phage indicates that approximately 500 pfu/0.05 μg of transgenic mouse genome DNA was observed, while a "–" plating efficiency indicates that less than 5 pfu/0.05 μg of transgenic mouse genome DNA was observed. Note also that (+) indicates that the mrr activity has not been confirmed in Y1088.

Figure 3:
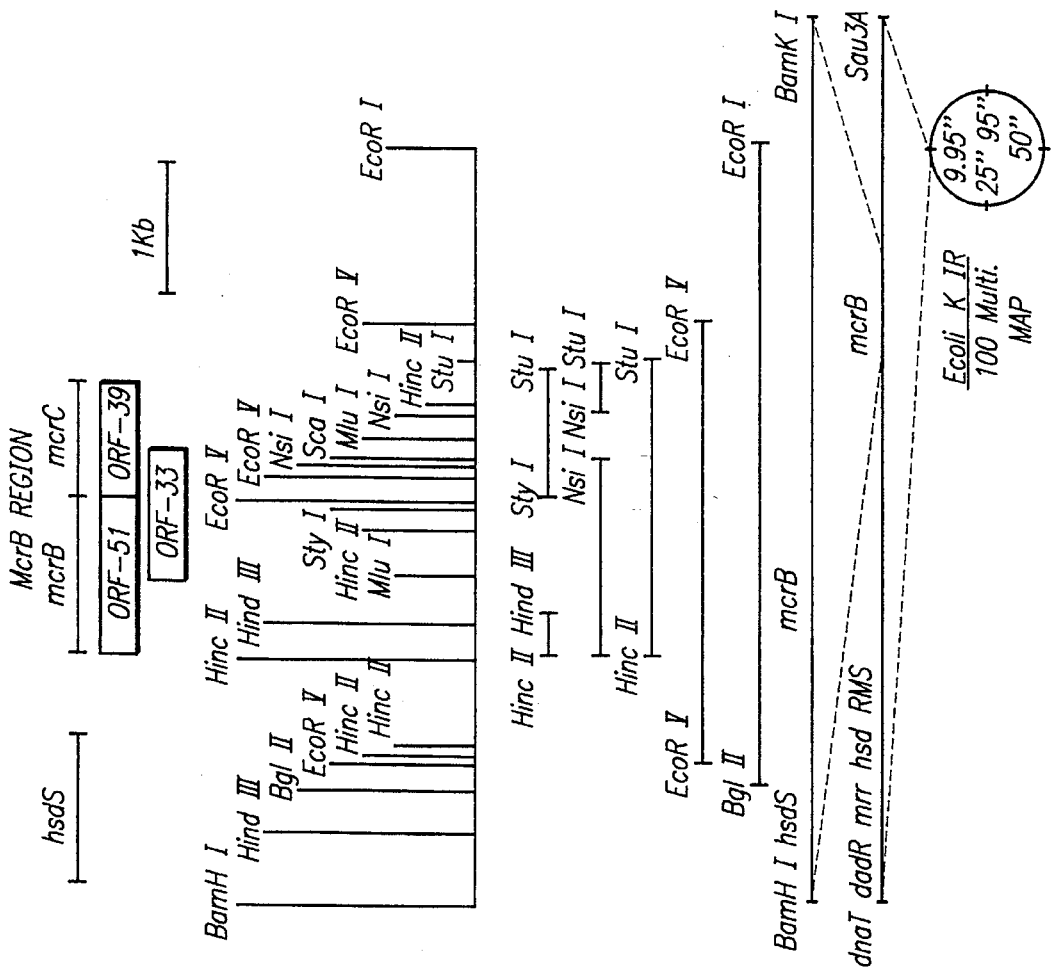
Figure 5:
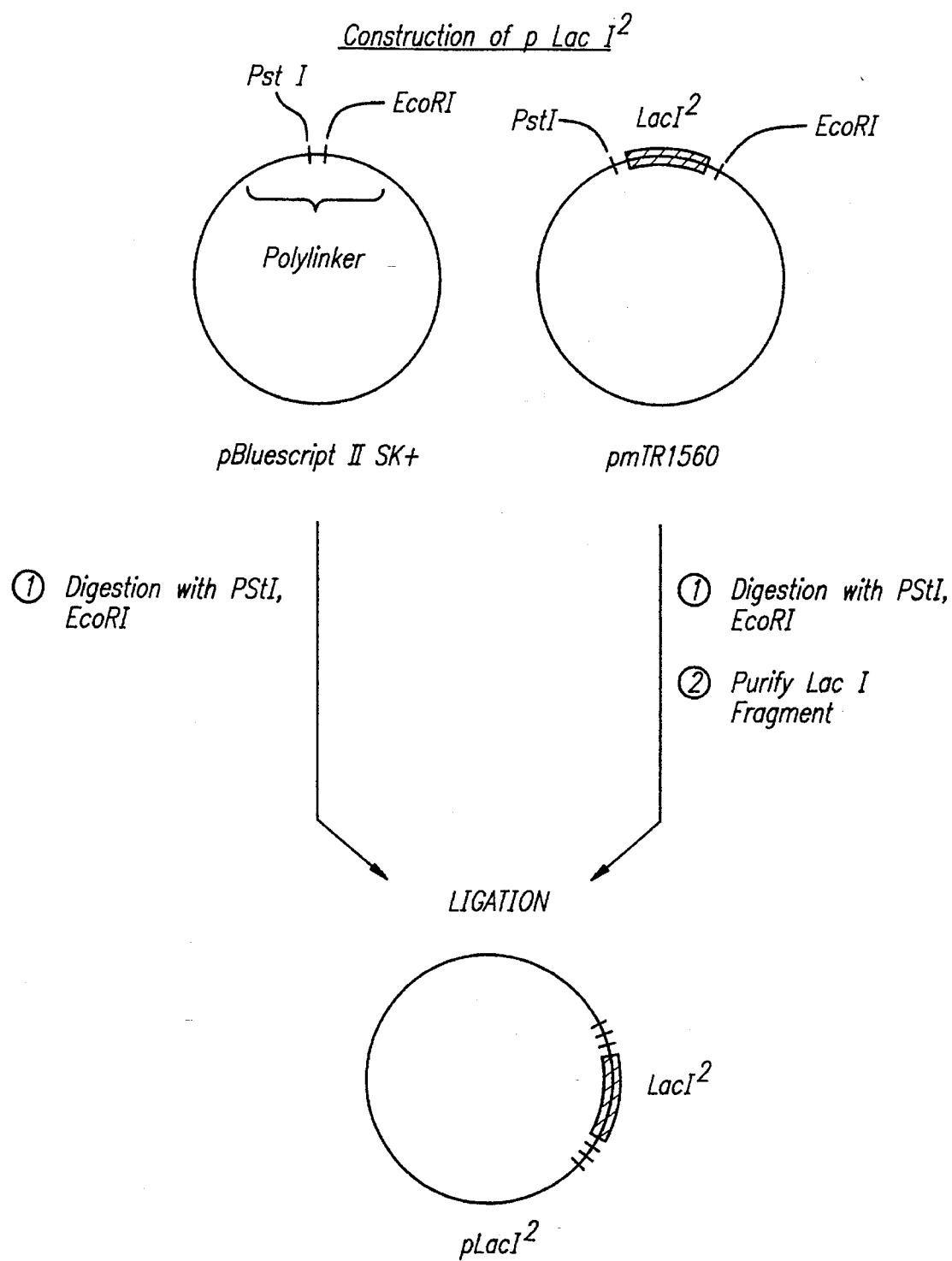
Figure 6:
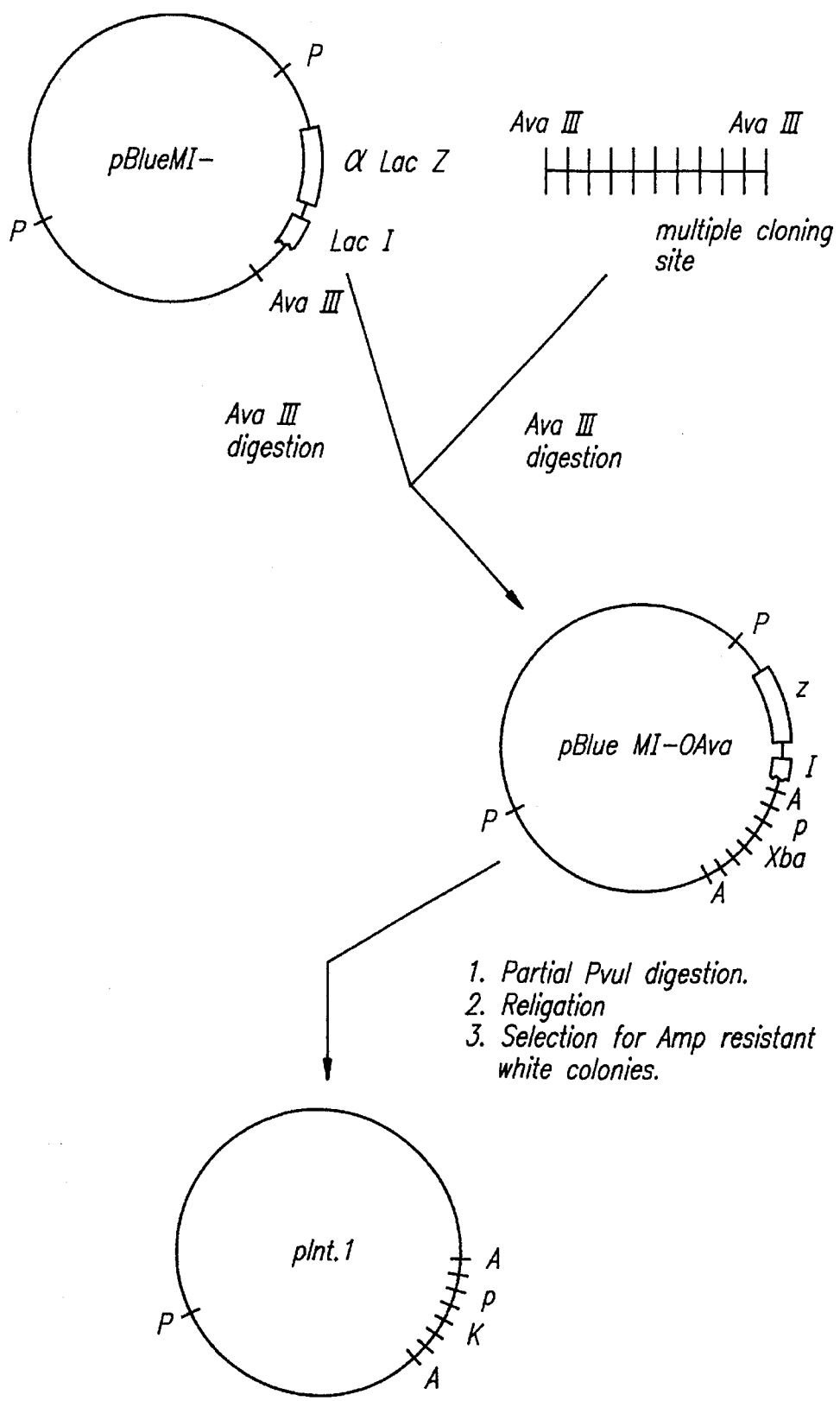
Figure 7:
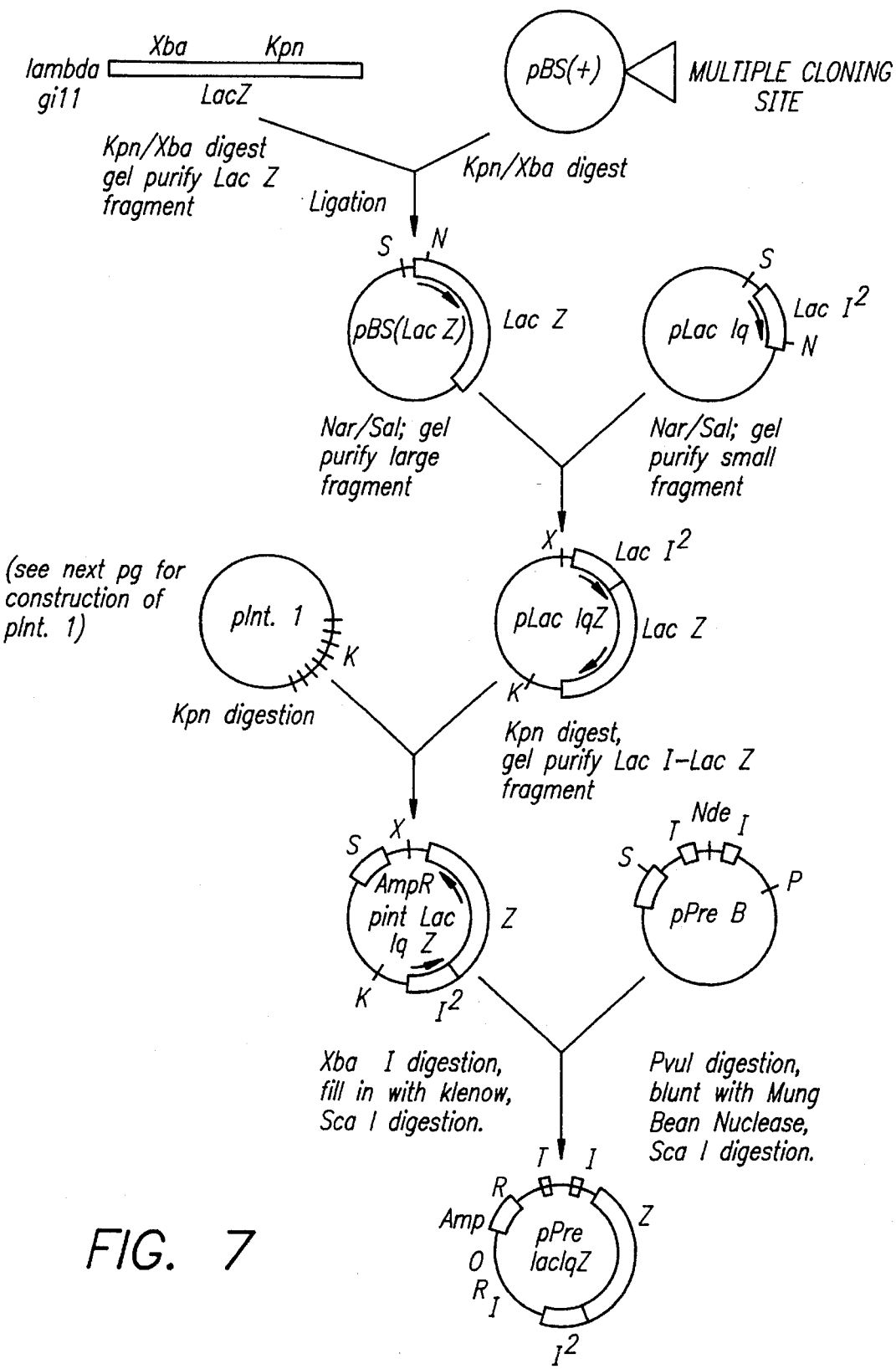
Figure 8:
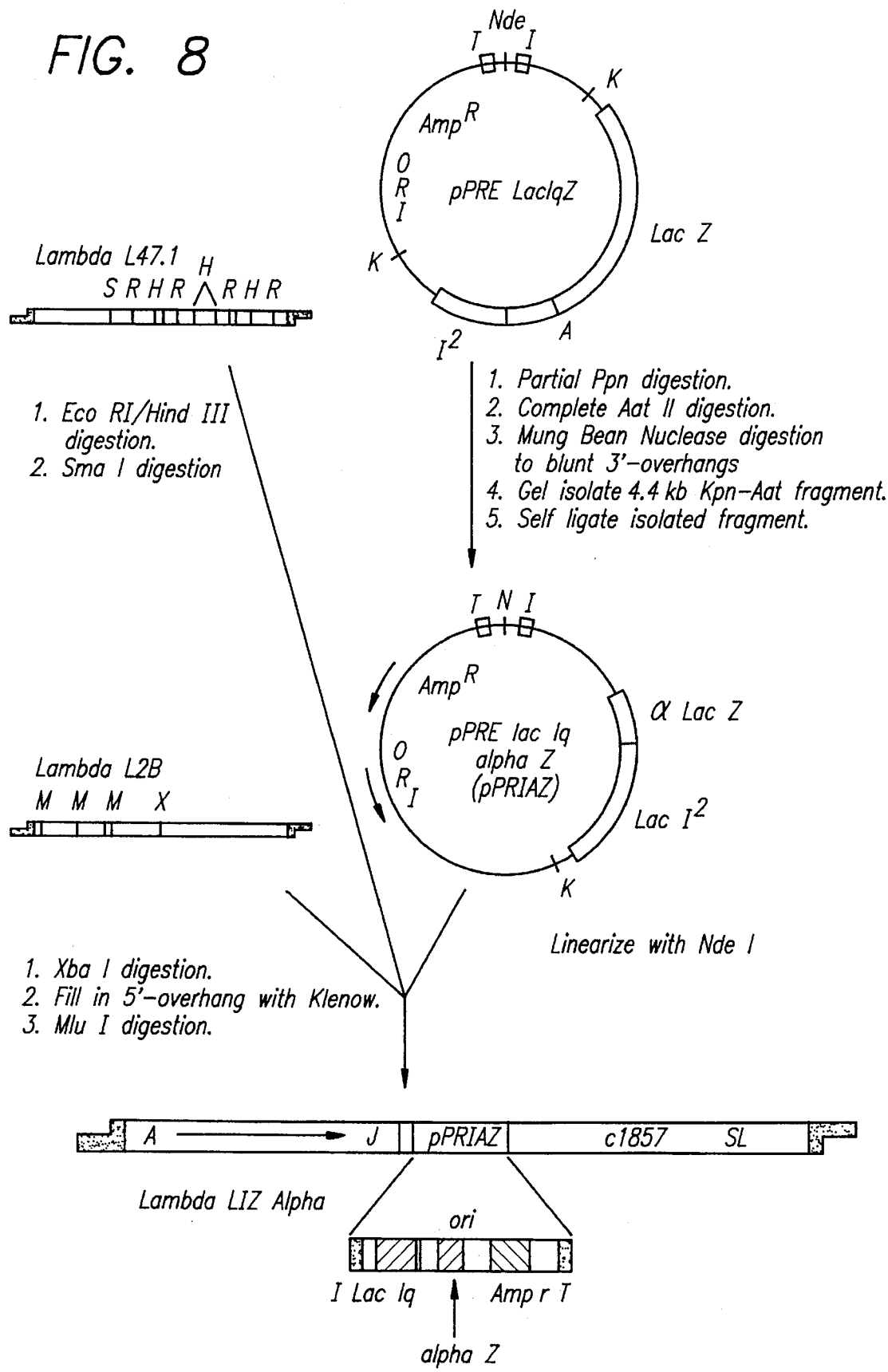

In order to determine more precisely the region of DNA responsible for the inhibition of dC-methylated lambda phage genome, the 98 minute region of *E. coli* K-12 LCK8 was cloned. A partial LCK8 genomic library was made in pOU61cos. (Knott, V. et al. *Nucleic Acid Res* 16:2601–2612 (1988)), packaged with Gigapack™ II XL (Stratagens, La Jolla, Calif.), and plated on *E. coli C*. Clones containing the 98 minute region were identified by colony hybridization using an oligo nucleotide (ATGAGTGCGGGGAAATTG) probe specific to the hsd region (Gough, J. A. et al., *J. Mol. Biol.* 166:1–19 (1983)). All clones were propagated in the host RR1-A when tested for plating efficiency of phage. As shown in FIG. 3, the activity was isolated to a 2.6 kb fragment containing the mcrB gene. The mcrB region including open reading frames (Ross et al., supra) is shown in the upper right hand corner of FIG. 3. The subclones corresponding to these groups are shown directly below. The table on the far left gives information pertaining to the DNA fragment shown on the right. (The restriction map depicted in FIG. 3, showing the location of the hsdS gene and adjacent McrB region of the *E. coli* K12 chromosome, is from Ross, T. et al., *J. Bact.* 171:1974–1981 (1989).)

The results in Table 1 support the observation that the restriction activities of the minute 98 region have a negative effect on rescue efficiency. To obtain high plating efficiencies, a complete deletion of the minute 98 mcrB region (mcrB through mrr) is preferred, as opposed to a small mutation of mcrB present in most commonly used mcrB-lab strains. This is because despite the mcrB-phenotype exhibited by these mcrB-strains (using ALuI methylase modified pBR 322 transformation as the assay (Ross, supra)), some inhibitory activity of the mcrB region remains. Complete deletion resulted in optimal efficiency, accounting for a greater than 1000-fold improvement in rescue efficiency using eukaryotic modified DNA.

While the use of mcrB deletion strains is described herein for use in mutagenesis testing and recovery of lambda phage DNA from mammalian cells, it is apparent that restriction system deficient strains may be used for other eukaryotic DNA cloning projects.

Of course, any number or variety of test DNA sequences or genes can be inserted between lambda cos sites. The in vitro packaging extract would still excise the DNA between the cos sites and package it into a lambda phage particle. Thus, a variety of recombinant lambda genomes or cosmids may be used for this excision event.

F. Construction of Shuttle Vector Systems for Rapid DNA Sequence Identification of Mutations in Test DNA Mutations evidenced by the production of white plaques resulting from disruption of the β-galactosidase (β-gal) gene are useful for determining the mutation rate of a mutagen, but give little information regarding the specific mutation within the DNA. In addition, analysis of the specific mutation is hampered somewhat by the size of the test β-gal gene (~3200 b.p.).

To help increase the effectiveness of the procedure, the target lambda phage can be made to provide a target gene with reduced size (lacI—1000 b.p.), and a rapid means with which the target gene is transferred from the lambda phaqe into plasmid vectors for sequence analysis.

Both the lacI and β-gal genes are inserted within a lambda vector, such that if the mutation occurs within the lacI gene, the repressor activity is lost allowing the β-gal gene to be expressed giving rise to blue plaques in the absence of IPTG. In the described embodiment, the lacI gene is positioned upstream of the alpha portion of the lacZ gene in the vector (Miller, J. H. and Reznikoff, W. S., *The Operon*, 2nd. Ed.

Cold Spring Harbor Laboratory, 1980, pp. 104–105). When the host *E. coli* (which is infected by the bacteriophage vector) provides the complementary portion of the lacZ gene (referred to as lacZΔM15) (Miller, J. H. and Reznikoff, W. S. supra), the gene products synthesized by these two partial genes combine to form a functional β-galactosidase protein (referred to as alpha-complementation) giving rise to blue plaques in the presence of Xgal when a mutation has occurred in the lacI gene or in the presence Xgal and IPTG when the lacI gene is not mutated. The ΔM15 portion of the lacZ gene provided by the host is provided either episomally (via a low copy number plasmid or F-factor) or stably integrated into the bacterial chromosome. The alpha portion of lacZ is used because 1) the β-gal protein formed by alpha-complementation is known to be weaker in activity than the contiguous protein, minimizing the possibility of background blue plaques due to inefficient repression by lacI, and 2) to provide a smaller and thus more easily characterized lacZ target should this gene be used in mutagenesis studies. The requirements of the host *E. coli* in this system are the following: lacI(−), latZΔM15, restriction(−). All cloning steps are outlined in the FIGS. 4 through 8 and are done using standard procedures (Sambrook, J. et al., *Molecular Cloning, A Laboratory Manual*, 2nd. Ed. Cold Spring Harbor Laboratory 1989).

The embodiment described utilizes the alpha portion of latz with lacI. The complete latz can also be used by providing a means to maintain complete repression by lacI until induction is desired. This can be done in a variety of ways including control of ΔM15 lacZ expression by a lambda specific promoter ($P_R'$) which prevents lacZ expression in the host *E. coli* until several minutes following infection by the bacteriophage, allowing lacI levels to build up to suitable levels to enable complete repression. Additionally, low levels of lac repressor can be maintained in the host to assist in repression by lacI until induction occurs, either by a mutation in lacI or by addition of IPTG to the system. A third alternative is to use an altered lacI gene which gives rise to a repressor protein with higher specific activity, thereby allowing stronger repression of β-galactosidase production.

The source of starting materials for the cloning procedures are as follows: the pBluescript II SK+ and SK−, pBS(+), lambda gt11, and lambda L2B are available from Stratagene Cloning Systems, La Jolla, Calif. Lambda L47.1 and pPreB: Short, J. M., et al., *Nucleic Acids Res.* 16:7583–7600. pMJR1560 is available from Amersham Corp., Arlington Heights, Ill.

Rapid sequencing of the mutagenized lacI gene within the lambda vector is facilitated by incorporating "lambda ZAP" excision sequence within the lambda vector. (Short, I. M. et al., *Nucleic Acids Res.* 16:7583–7600 (1988)). Lambda ZAP is a lambda phage vector which permits in vivo excision of inserts from the lambda vector to a plasmid. This is possible because the lambda phage contains the two halves of an f1 bacteriophage origin of replication. In the presence of proteins supplied by f1 helper phage, all DNA present between the two partial f1 origins is automatically excised from the lambda phage. The two halves come together to form an intact f1 origin. The resulting phagemid contains a Col E1 origin of replication and an ampicillin resistance gene, thus the insert is effectively subcloned into a plasmid vector. All sequences between the two partial f1 origins are excised as a plasmid within hours.

In the mutation analysis vector, these f1 origins are positioned so that the lacI gene can be automatically excised from the lambda vector following mutagenesis of the mouse and recovery of the lambda phage from the mouse genomic DNA. Following this conversion from phage to plasmid, the insert may be rapidly sequenced or characterized by other known methods. Characterization of a large number of mutations within the lacI gene can be completed within 3 days following isolation of mouse genomic DNA, as opposed to several months using standard techniques.

In the example described herein, a lambda ZAP is used to convert the test DNA inserts from integration in the lambda vector to a plasmid. Other systems may also be used which allow excision and recircularization of a linear sequence of DNA thereby providing a rapid means with which the test DNA sequence may be transferred from the phage to a form suitable for analysis. Such other systems include, but are not limited to, the use of FLP-mediated (Senscoff, J. et al., *Proc. Natl. Acad. Sci. U.S.A.*, 82:7270–7274 (1985); Jayaram, M., *Proc. Natl. Acad. Sci. U.S.A.*, 82:5875–5879 (1985); McLeod, M., *Mol. Cell. Biol.*, 6:3357–3367 (1986); Lebreton, B. et al., *Genetics*, 118:393–400 (1988)) or Cre-lox site specific recombination techniques (Hoess, R. et al., *J. Mol. Biol.* 181:351–362 (1985); Hoess, R. et al., *Proc. Natl. Acad. Sci. U.S.A.* 81:1026–1029 (1984)).

The embodiments described above utilize the *E. coli* beta-galactosidase gene as a test DNA sequence, which allows phenotypes that are positive and negative for mutation to be observed. Other potential test DNA sequences include (but are not limited to): the lac I repressor, the cI repressor, any antibiotic resistance gene sequence (ampicillin, kanamycin, tetracycline, neomycin, chloramphenicol, etc.), the lambda red and gam gene sequences, a thymidine kinass gene sequence, a xanthine-guanine phosphoribosyl transferase gene sequence, sequences that code for restriction enzymes or methylation enzymes, a gene sequence that codes for luciferase, and/or a tRNA stop codon or frameshift suppressor gene sequence.

Figure 2:
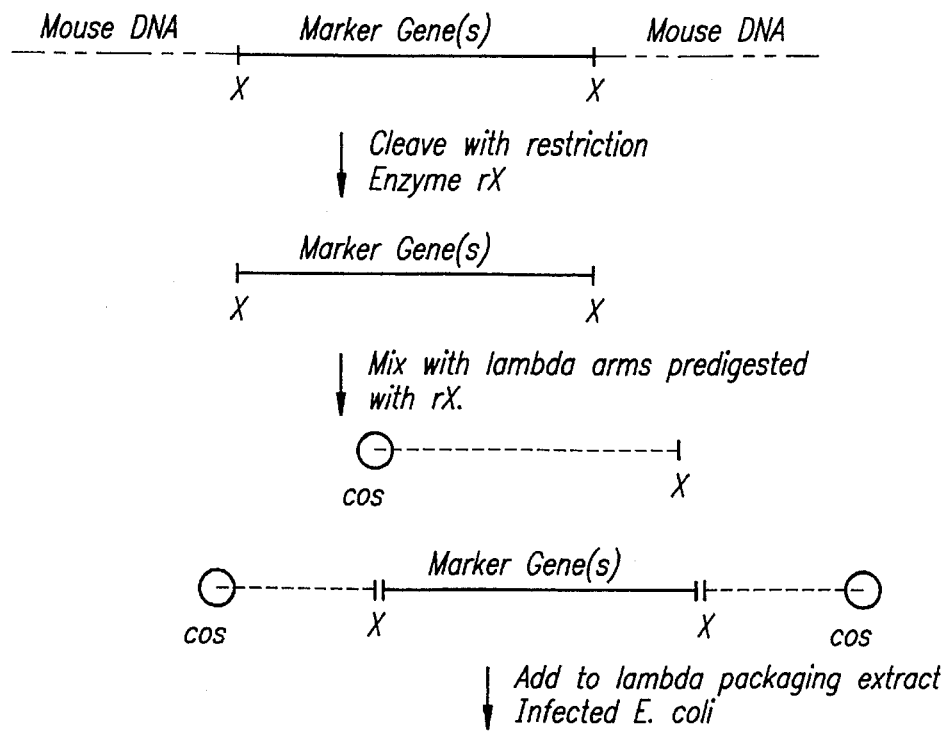

Even more general models can be made that eliminate the cos sites, although the excision mechanism now becomes different. By bracketing the test DNA sequence(s) with convenient restriction sites, as shown in FIG. 2, the test sequence(s) can be separated away from the mouse DNA with restriction enzymes and subsequently ligated with lambda or cosmid vectors which contain cos sites or if the test sequence is linked to a replication origin it can be transformed directly. Background can be reduced in such a system by including with the test DNA sequences a sequence that is necessary for lambda phage replication, which is then cloned with the test DNA sequence into a lambda genome deficient or defective in that sequence.

We claim:

1. A method for testing the mutagenic potential of an agent comprising:

(a) exposing a transgenic mouse to an agent to be tested, said transgenic mouse comprising somatic and germ cells containing an integrated transgenic test DNA sequence, said test DNA sequence being flanked by the cos sites of a lambda bacteriophage and recoverable from said cells via said cos sites, the expression of said test DNA sequence being capable of detection in *E. coli* by bioassay, wherein said test DNA sequence encodes a protein selected from the group consisting of LacZ and LacI;

(b) isolating a sample of genomic DNA from said exposed transgenic mouse;

(c) treating said sample of genomic DNA with a lambda bacteriophage packaging extract to excise said integrated transgenic test DNA sequence and then package said excised test DNA sequence;

(d) infecting *E. coli* with said packaged test DNA sequence;

(e) determining by bioassay in said infected *E. coli* the frequency of mutation of said test DNA sequence.

2. A method according to claim 1, wherein said test DNA sequence encodes LacZ.

3. A method according to claim 1, wherein said test DNA sequence encodes LacI.

4. A method according to claim 1, wherein said *E. coli* strain is restriction system deficient.

5. A method according to claim 1, wherein the lambda phage packaging extract is restriction system deficient.

6. A method according to claim 5 wherein said restriction system is selected from the group consisting of hsdR, mcrA, and mcrB.

* * * * *

UNITED STATES PATENT AND TRADEMARK OFFICE
CERTIFICATE OF CORRECTION

PATENT NO. : 5,589,155
DATED : December 31, 1996
INVENTOR(S) : Sorge, *et al.*

It is certified that error appears in the above-indentified patent and that said Letters Patent is hereby corrected as shown below:

On the cover page of the issued patent at number [73] the Assignee is identified as "Union Bank of California, N.A., San Francisco, Calif." The Assignee should read: "Stratagene."

Signed and Sealed this

Twenty-second Day of July, 1997

Attest:

BRUCE LEHMAN

*Attesting Officer*  *Commissioner of Patents and Trademarks*